(12) United States Patent
Aoki et al.

(10) Patent No.: US 7,553,612 B2
(45) Date of Patent: Jun. 30, 2009

(54) METHOD FOR CRYOPRESERVING MICROENCAPSULATED LIVING ANIMAL CELLS ENCLOSED IN IMMUNOISOLATION MEMBRANES, SUCH MICROENCAPSULATED LIVING ANIMAL CELLS IN IMMUNOISOLATION MEMBRANES, AND BIOHYBRID ARTIFICIAL ORGAN MODULES USING SUCH MICROENCAPSULATED LIVING ANIMAL CELLS IN IMMUNOISOLATION MEMBRANES

(75) Inventors: Takeshi Aoki, Setagaya-ku (JP); Mitsuo Kusano, Ohta-ku (JP); Yoshinori Shimizu, Ohta-ku (JP); Tomotake Koizumi, Shinagawa-ku (JP); Daisuke Yasuda, Ohta-ku (JP); Yoshihiko Izumida, Chiyoda-ku (JP); Noriyuki Murai, Ohta-ku (JP); Zhenghao Jin, Shinagawa-ku (JP); Yasuna Kobayashi, Shinagawa-ku (JP); Hirohisa Kato, Shinagawa-ku (JP); Luchun Hua, Shanghai (JP)

(73) Assignee: Showa University, Tokyo (JP)

( * ) Notice: Subject to any disclaimer, the term of this patent is extended or adjusted under 35 U.S.C. 154(b) by 408 days.

(21) Appl. No.: 11/082,055

(22) Filed: Mar. 17, 2005

(65) Prior Publication Data

US 2005/0265979 A1    Dec. 1, 2005

(30) Foreign Application Priority Data

Mar. 24, 2004    (JP)    ............................. 2004-086822

(51) Int. Cl.
*A01N 1/02*    (2006.01)
(52) U.S. Cl. ....................... 435/1.3; 424/93.7
(58) Field of Classification Search ................ 424/93.7; 435/1.3
See application file for complete search history.

(56) References Cited

U.S. PATENT DOCUMENTS 6,303,355 B1 * 10/2001 Opara ......................... 435/178

OTHER PUBLICATIONS

Dixit et al., "Cryopreserved Microencapsulated Hepatocytes-Transplantation Studies in Gunn Rats," Transplantation, vol. 55, No. 3, Mar. 1993, pp. 616-622.

Matsumoto et al., "Microencapsulation for Improvement of the Viability in Cryopreserved Cells," Nippon Mechanics Academic Society Annual Conference Papers, No. 99-1, 1999, pp. 309-310.

Matsumoto et al., "Improvement in the Viability of Cryopreserved Cells by Microencapsulation," Transactions of the Japan Society of Mechanical Engineers, 2001, vol. 67, No. 654, pp. 276-283 (Advertisement "EnLiten & EnVideo")(Advertisement "Quick Therm/Quick Welder").

Cai et al., "Development and Evaluation of a System of Microencapsulation of Primary Rat Hepatocytes," Hepatology, vol. 10, No. 5, Nov. 1989, pp. 855-860.

Kobayashi et al., "Hybrid bioartificial liver: establishing a reversibly immortalized human hepatocyte line and developing a bioartificial liver for practical use," Journal of Artificial Organs, vol. 6, No. 4, 2003, pp. 236-244.

Adham, "Extracorporeal Liver Support: Waiting for the Deciding Vote," ASAIO Journal, 2003, pp. 621-632.

Watanabe et al., Clinical Experience With a Bioartificial Liver in the Treatment of Severe Liver Failure, Annals of Surgery, vol. 225, No. 5, May 1997, pp. 484-494.

Mizumoto et al., "Liver Regeneration Using a Hybrid Artificial Liver Support System," Artificial Organs, International Society for Artificial Organs, vol. 28, No. 1, 2004, pp. 53-57.

Yoshiba et al., "Favorable Effect of New Artificial Liver Support on Survival of Patients with Fulminant Hepatic Failure," Artificial Organs, International Society for Artificial Organs, vol. 20, No. 11, 1996, pp. 1169-1172.

* cited by examiner

*Primary Examiner*—Jon P Weber
*Assistant Examiner*—Kailash C Srivastava
(74) *Attorney, Agent, or Firm*—Oliff & Berridge, PLC

(57) ABSTRACT

A method is disclosed for cryopreserving living animal cells in immunoisolation membranes, including: (1) cutting out a living organ from an animal, (2) digesting the cutout organ into the discrete living animal cells and separating the discrete cells, (3) suspending the separated cells in a solution of sodium chloride containing sodium alginate and collagen, (4) forming microcapsules of the living animal cells by using the resulting suspension, (5) forming immunoisolation membranes around outer surfaces of the microcapsules of the living animal cells by covering the outer surfaces with alginate-(poly-L-lysine) and thereby obtaining the living animal cells enclosed in the immunoisolation membranes, (6) suspending the resulting living animal cells enclosed in the immunocapsules in a cell damage-preventing solution, and (7) immediately freezing the thus obtained suspension with liquid nitrogen.

4 Claims, 11 Drawing Sheets
(11 of 11 Drawing Sheet(s) Filed in Color)

METHOD FOR CRYOPRESERVING MICROENCAPSULATED LIVING ANIMAL CELLS ENCLOSED IN IMMUNOISOLATION MEMBRANES, SUCH MICROENCAPSULATED LIVING ANIMAL CELLS IN IMMUNOISOLATION MEMBRANES, AND BIOHYBRID ARTIFICIAL ORGAN MODULES USING SUCH MICROENCAPSULATED LIVING ANIMAL CELLS IN IMMUNOISOLATION MEMBRANES

BACKGROUND

The present invention relates to a method for cryopreserving microencapsulated living animal cells enclosed in immunoisolation membranes, such microencapsulated living animal cells enclosed in the immunoisolation membranes, and biohybrid artificial organ modules using such microencapsulated living animal cells enclosed in the immunoisolation membranes. In particular, the present invention relates to a method for cryopreserving microencapsulated living hepatocytes in immunoisolation membranes, such microencapsulated living hepatocytes in the immunoisolation membranes, and biohybrid artificial organ modules using such microencapsulated living hepatocytes in the immunoisolation membranes.

Although acute hepatic failure has been still recognized as a serious disease among various ones, high survival rates have been recently reported for patients suffering high fulminant hepatic failure according to an artificial liver-assisting method based on a mechanically blood-purifying method in which plasmaphoresis and blood filtration/osmosis are combined. Thus, results on such treatments will be largely expected in the future. See (1) Yoshiba M, et al., "Favorable effect of new artificial liver support on survival of patients with fulminant hepatic failure." Artif Organ. 20, pp. 1169-72, 1996. In Europe, hybrid type artificial liver modules have been clinically applied, aiming at further assistance of the liver function, and some of them succeeded as bridge-like or interface uses. See (2) Watanabe F D, Mullon C J, Hewitt W R, Arkadopoulos N, kahaku E, Eguchi S, Khalili T, Arnaout W. Shackleton C R, Rozga J, Solomon B, Demetriou A A; "Clinical experience with a bioartificial liver treatment of severe liver failure" and (3) Adam M., "Extracorporeal liver support: Waiting for the deciding vote." ASAIO J. 49, 2003, pp. 621-632. In Japan, epoch-making artificial liver modules have been researched and developed. See (4) Mizumoto H, Funatsu K., "Liver regeneration using a hybrid artificial liver support system." Artif Organs. 28, 2004, pp. 53-57 and (5) Kobayashi N, Okitsu T, Nakaji S, Tanaka N., "Hybrid bioartificial liver: establishing a reversibly immortalized human hepatocyte line and developing a bioartificial liver for practical use." However, there may be problems in infection with swine retrovirus, overcoming of immunological reactions, adjustment of the number of hepatocytes in reactors, securement of cell sources, establishment of long-term cryopreserving methods, etc., and new artificial livers which can be clinically applied and exceed the existing treatment method for the acute hepatic failure have not been developed yet. See references (1) to (5) listed above.

It has been a common technical knowledge in the art that cells from living animal organs are slowly cooled, since rapid cooling resulting in damages of such cells must be avoided. The conventional recognition is that rapid freezing make a cell-suspended liquid form needle-shape crystals, so that thus tips of formed needle-shaped crystals pierce cells into death.

Thus, according to some conventional techniques, hepatic cells are microencapsulated, and cryopreserved in a cryogenic freezer which can generally cool down to −80° C., while the cooling rate is being measured and controlled to 0.1 to 10° C./min, 0.1 to 100° C./min, or the like with a T thermocouple or the like with a voltage being controlled according to a program. Alternatively, based on the above conventional technical recognition, the cells are maintained at −70° C. for 24 hours after slow cooling in the cryogenic freezer, and then they are cooled with liquid nitrogen (freezing point: −196° C.). See references (6) to (9) below:

(6) Transplantation, 1993, Vol. 55, No. 3, pp. 616 to 622.

(7) Nippon Mechanics Academic Society Annual Conference Papers, 1999, Vol. 1999, No. 2, pp. 309-310.

(8) Nippon Mechanics Academic Society Papers B, 2001, Vol. 67, No. 654, pp. 580 to 587.

(9) Bioengineering Academic Conference Papers 1999, Vol. 11, pp. 96 to 97.

(10) Hepatology, 1989, Vol. 10, No. 5, pp. 855 to 860.

When hybrid type artificial organs such as hybrid type artificial livers and the like are considered, it is important to prevent immunological reactions. In addition, it is desirable that the function of the cells can be kept at a high level and a sufficient amount of such cells can be preserved for a long time. In order to solve the above problems, the present inventors tried to establish a method for cryopreserving living animal cells enclosed in immunoisolation membranes and then succeeded.

SUMMARY

In order to solve the above problems, the present invention is to provide a method for cryopreserving living animal cells in immunoisolation membranes, comprising: (1) cutting out a living organ from an animal, (2) digesting the cutout organ into the discrete living animal cells and separating the discrete cells, (3) suspending the separated cells in a solution of sodium chloride containing sodium alginate and collagen, (4) forming microcapsules of the living animal cells by using the resulting suspension, (5) forming immunoisolation membranes around an outer surface of each of the microcapsules of the living animal cells by covering the outer surfaces with alginate-(poly-L-lysine) and thereby obtaining the living animal cells enclosed in the immunoisolation membranes, (6) suspending the resulting living animal cells enclosed in the immunocapsules in a cell damage-preventing solution, and (7) immediately freezing the thus obtained suspension with liquid nitrogen. The term "living organ from an animal" includes the entire organ or a part of the organ cut out from the living animal or the animal judged to be brain-dead. As to the alive human being, it is a matter of course that such an organ is allowed to be cut from it, provided that the life of the human being is not subjected to heavy danger or dead. The term "the animal judged to be brain-dead" means that the organ is still active to be used in the claimed invention.

In the method for cryopreserving the living animal cells in the immunoisolation membranes according to the present invention, the living animal organ may be a human liver or a rat liver. Although the living animal cells in the method for cryopreserving the living animal cells in the immunoisolation membranes according to the present invention are not limited to any particular living animal organs, human livers and rat livers are particularly desired as biohybrid artificial organ modules for its application, because the acute hepatic failure has been still recognized as a serious disease.

In the method for cryopreserving the living animal cells in the immunoisolation membranes according to the present invention, "Dulbecco's modified Eagle medium" (DMEM) (a low concentration of glucose, L-glutamine, 25 mM HEPES, 110 mg/L sodium pyruvate, and pyridoxine hydrochloride, which is publicly known after having been described in Cat. No. 12320-032, Lot No. 1181791 (GIBCO)) and which contains fetal bovine serum (FBS) and/or dimethylsulfoxide (DMSO), is particularly suitable as the cell damage-preventing solution. The concentration of each of FBS and DMSO contained in DMEM may be 10% by volume (the concentration in DMEM culture liquid: for example, 1 cc FBS, 1 cc DMSO and 8 cc DMEM). Such concentrations may be considered particularly suitable for the method for cryopreserving the living animal cells in the immunoisolation membranes state according to the present invention.

The present invention is also to provide a cryopreserved cell mixture comprising microencapsulated living animal cells enclosed in immunoisolation membranes and a cell damage-preventing solution in which the living animal cells enclosed in the immunoisolation membranes are suspended, said microencapsulated living animal cells enclosed in the immunoisolation membranes comprising microcapsules each containing a number of living animal cells, and the immunoisolation membranes being made of alginate-(poly-L-lysine) and covering said microcapsules, wherein the resulting suspension of the living cells in the cell damage-preventing solution is cryopreserved immediately with liquid nitrogen after the suspension.

In the cryopreserved mixture comprising the microencapsulated living animal cells enclosed in immunoisolation membranes according to the present invention, as mentioned above in connection with the method for cryopreserving the living animal cells in the immunoisolation membranes state according to the present invention, the living animal organ may be a human liver or a rat liver, and the DMEM containing the FBS and/or DMSO is particularly suitable as the cell damage-preventing solution.

The present invention is also to provide a biohybrid artificial organ module comprising a radial flow bioreactor, and living animal cells enclosed in immunoisolated membranes filled in the bioreactor, said living animal cells enclosed in immunoisolated membranes being obtained by unfreezing the above-cryopreserved living animal cells. The biohybrid artificial organ module may be a biohybrid artificial liver module. The animal living cells may be originated from a human liver or a rat liver. After being unfrozen, the microcapsules are gravitationally precipitated without filtration and the supernatant liquid (the cell damage-preventing solution) is sucked out. Thereafter, the precipitate is washed with phosphate buffer saline (PBS) three times. The washing is effected in such a manner that PBS is poured and then the supernatant liquid is disposed of after the microcapsules are gravitationally precipitated. The washed microcapsules are filled into the radial flow bioreactor. After the washing, the immunoisolation membranes are retained on the living animal cells.

The following effects are obtained in the method for cryopreserving the living animal cells in the immunoisolation membranes according to the present invention.

(1) According to the method for cryopreserving the living animal cells in the immunoisolation membranes of the present invention, a living organ is cut out from an animal, the cutout organ is digested into the discrete living animal cells, the cells are separated and suspended in a solution of sodium chloride containing sodium alginate and collagen, microcapsules of the living animal cells are formed by using the resulting suspension, immunoisolation membranes are formed around outer surfaces of the microcapsules of the living animal cells by covering the outer surfaces with alginate-(poly-L-lysine) and thereby the living animal cells enclosed in the immunoisolation membranes are obtained. Then, the resulting living animal cells are suspended in the immunocapsules in a cell damage-preventing solution, and the thus obtained suspension is immediately cryopreserved with liquid nitrogen. As compared with the conventional method, therefore, the invention method, which is contrary to the conventional common technical knowledge and anticipation that the cells are damaged or dead when they are rapidly cryopreserved directly with liquid nitrogen, can inexpensively cryopreserve the living animal cells in the immunoisolation membranes by simpler operations.

(2) As mentioned later, according to the invention method, the living animal cells in the immunoisolation membranes can be cryopreserved for a long time without losing their cellular function. Accordingly, the living animal cells in the immunoisolation membranes can be clinically applied over a wide range for a long time.

(3) According to the method for cryopreserving the living animal cells in the immunoisolation membranes of the present invention, since no complicated chemicals are used, the unfrozen living animal cells in the immunoisolation membranes can be easily clinically applied, while suppressing clinically harmful influences.

(4) The living animal cells in the immunoisolation membranes in the cryopreserved state according to the present invention can be expected to function as an extracorporeal internal organ-assisting system such as an extracorporeal liver-assisting system by combining the living animal cells in the immunoisolation membranes cryopreserved with the radial flow bioreactor.

These and other objects, features and advantages of the invention will be appreciated upon reading of the following description of the invention with the understanding that some modifications, variation or changes could be made by the skilled person in the art to which the invention pertains without departing from the spirit of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

For a better understanding of the invention, reference is made to the attached drawings, wherein.

DETAILED DESCRIPTION OF EMBODIMENTS

Figure 1:
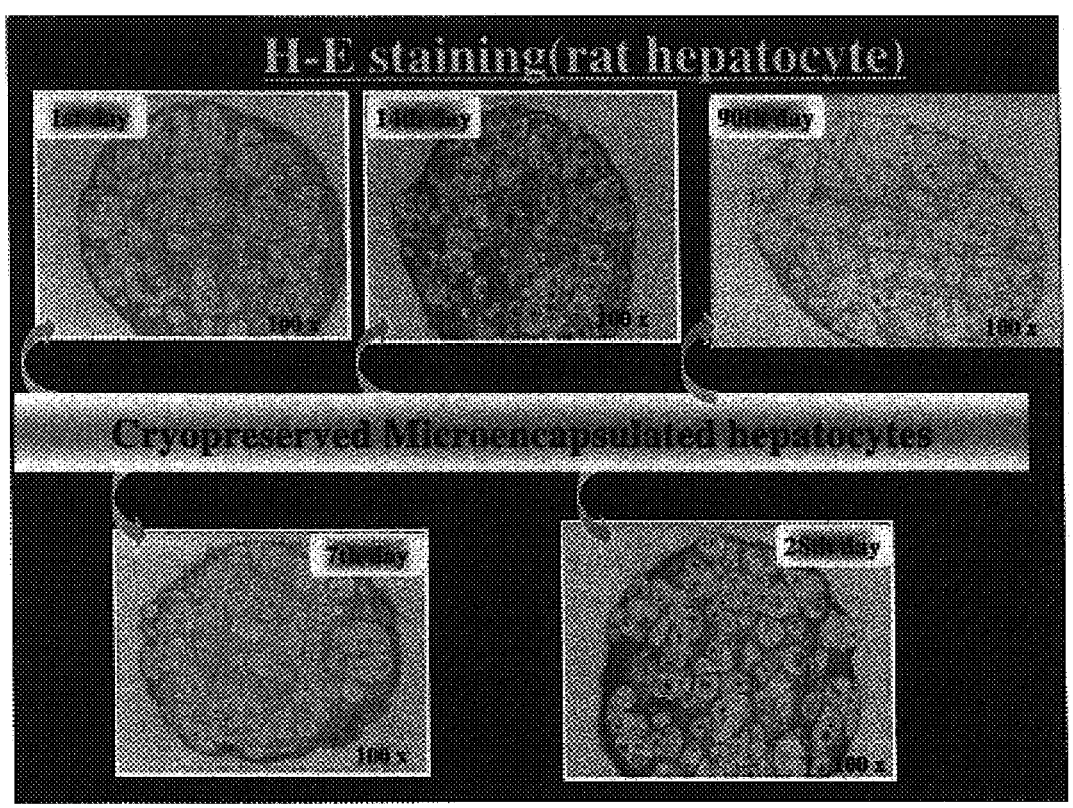
FIG. 1 gives H-E (Hematoxylin & Eosin) staining test results with photographs showing H-E stained rat cryopreserved microencapsulated hepatocytes (1st day, 7th day, 14th day, 28th day and 90th day), which show that the rat hepatocytes in the immunoisolation membrane survived after being cryopreserved for 90 days.

In the following, embodiments of the present invention will be explained in more detail.

(1) Digestion

In the method for cryopreserving the living animal cells enclosed in the immunoisolation membranes according to the present invention, a cutout organ such as a human liver or a rat liver can be digested into discrete cells in two stages with collagenase. Since such a digesting treatment is publicly known, detailed explanation thereon is omitted, but briefly made.

First, whole blood is expelled from the cutout organ (including a part of such an organ) by canulation (whole perfusion) with ethylenediaminetetraacetic acid (EDTA), and fresh EDTA is further flown to replace the whole blood with EDTA. Then, the organ is digested by adding collagenase thereto. Thereby, the living animal cells such as human organ cells or rat organ cells are digested into discrete cells. The discrete living organ cells are subjected to a centrifugal separator, so that precipitated living animal cells are separated from the remainder containing no actual cells as a supernatant liquid. After the supernatant liquid is removed, the precipitated living animal cells are microencapsulated.

In the case of the rat, the organ was subjected to perfusion, while being living under anesthesia without cutting out the organ. In the case of the human being, the organ was cut out and used.

(2) Microencapsulation and Enclosing the Microencapsulated Living Animal Cells with the Immunoisolation Membranes The digested and separated living animal cells (for example, artificial hepatocytes, rat hepatocytes) are microencapsulated with alginate salt/poly-L-lysin, the cells were suspended in DMEM containing 10% FBS and 10% DMSO, and the suspension containing the microcapsules is cryopreserved with liquid nitrogen.

(2-1) Microencapsulation

Microencapsulation is effected according to a syringe extrusion process described in Cai Z H, Shi Z Q, Sherman M, Sun A M. Hepatology, 1989, 10(5), pp. 855-860. Living protopathic animal cells such as protopathic hepatocytes are mixed and suspended in an aqueous solution of sodium chloride containing sodium alginate and collagen I type, the mixed gel liquid is filed in a injection syringe, for example, and the gelled liquid is dropwise added into an aqueous solution of potassium chloride by air jet system, thereby microencapsulating the drops of the gelled liquid. A number of the discrete living animal cells are contained in each of the microcapsules.

(2-2) Covering the Microencapsulated Living Animal Cells with the Immunoisolation Membranes After the microcapsules are washed with 2-(N-cyclohexylamino)ethane sulfonic acid (CHES; Sigma Co., Ltd), an aqueous solution of potassium chloride and an aqueous solution of sodium chloride, the resulting spherical microcapsules are covered with poly-L-lysin (Sigma Co., Ltd.), which are then washed with the CHES aqueous solution, the potassium chloride aqueous solution and the sodium chloride aqueous solution successively in this order. The resulting microcapsules are exposed to sodium alginate, thereby covering the outer surfaces of the microcapsules with filmy immunoisolation membranes. A number of gelled separated living animal cells are contained inside each of the microcapsules in the gel state. The gel is formed with collagen I type gelled with sodium alginate, and the immunoisolation membrane-enclosed cells are dispersed in the gel.

(3) Cryopreserving

The immunoisolation membrane-enclosed living animal cells obtained by covering the outer surfaces of the microencapsulated with the immunoisolation membranes are suspended in the cell damage-preventing solution, and the resulting suspension is immediately cryopreserved with liquid nitrogen. As mentioned above, DMEM containing FBS and DMSO may be used as the cell damage-preventing solution.

The cellular activity and the function of the hepatocytes decrease with the lapse of time. The word "immediately" means that the cellular activity and the function of the hepatocytes are prevented from decreasing by carrying out the separation step, the suspending step, the immunoisolation membrane-forming step and the cell damage-preventing solution suspending step as soon as possible and then cryopreserving the hepatocytes in liquid nitrogen as soon as possible. For example, the cells are cryopreserved with liquid nitrogen within 10 minutes after the cells are suspended in the cell damage-preventing solution.

(4) Unfreezing

When the immunoisolation membrane-enclosed living animal cells are to be used, the cryopreserved cells are pulled up from the liquid nitrogen, and spontaneously unfrozen in a water bath at 37° C., for example. Then, as mentioned above, after the precipitation step, the supernatant liquid-removing step and the washing step, the resulting immunoisolation membrane-enclosed living animal cells are filled in the radial bioreactor.

(5) Artificial Organ Module

Blood is continuously taken out from a living patient body by pump, and first separated into a blood cell component and a plasma component, and the plasma component is passed through the biohybrid artificial organ module composed of the radial flow bioreactor filled with the unfrozen immunoisolation membrane-enclosed living animal cells. Alternatively, the blood of the patient is passed directly through such a biohybrid artificial organ module. Thereby, the plasma is circulated into the patient body after treatment by given cellular metabolism.

In the following, the present invention will be explained based on Examples.

(Human Hepatocytes, Rat Hepatocytes)

After animal hepatocytes such as human hepatocytes or rat hepatocytes were digested into discrete living animal cells by two-stage digestion with collagenase and EDTA. Then, the discrete hepatocytes were mixed with a percoll density gradient solution, and the activity of the cells was judged with a typan blue exclusion, which revealed that the survival rate of the cells was not less than 95%.

(Culturing of Microencapsulated Hepatocytes)

Several million of microencapsulated hepatocytes were manually divided into equal portions, each of which was added into DMEM reinforced with 10% FBS, 0.2% bovine serum albumin, 20 mM HEPES, 25 mM $NaHCO_3$, 1 mg/ml galactose, 30 μg/ml L-proline, 0.5 mM glutamine, 10-7 M dexamethazone, 10 mM nicotinamide, 0.5 μg/ml ITS51500, 20 ng/ml EGF, 0.1 mM L-ascorbic acid 2-phosphate (Acs-2P), and 100 μg/ml penicillin, 50 μg/ml streptomycin. Each of the resulting suspensions was placed onto a suspension culturing tray (60 mm in diameter×15 mm, Corning Co., Ltd., NY), and then cultured for 28 days. The cell culture was maintained at 37° C. in wet air containing 5 weight % $CO_2$. Each of the following experiments was repeated three times with use of the cells from different hepatocytes.

Experiment 1

The hepatocytes were microencapsulated by the alginate/poly-L-lysine method, and then suspended in DMEM containing 10% FBS and 10% DMSO. The suspension was immediately placed in liquid nitrogen and cryopreserved. The cryopreserved hepatocyte microcapsules in the immunoisolation membrane were unfrozen with the lapse of time in a water bath at 37° C., and histogenetic evaluations (H-E, PAS (Periodic Acid Schiff Staining), ALB, and drug-metabolizing capacity (cytochrome P450IIIA2, 9)) were examined for them. The microencapsulated rat hepatocytes were unfrozen 1st day, 7th day, 14th day, 28th day and 90th day after beginning the cryopreservation, and their cell activity was examined. They exhibited "positive" for ALB and PAS, and expression of OAT2 and CYP450IIIA2 and 9 was observed. It was also revealed that the cryopreserved microencapsulated rat hepatocytes maintained viability.

Figure 2:
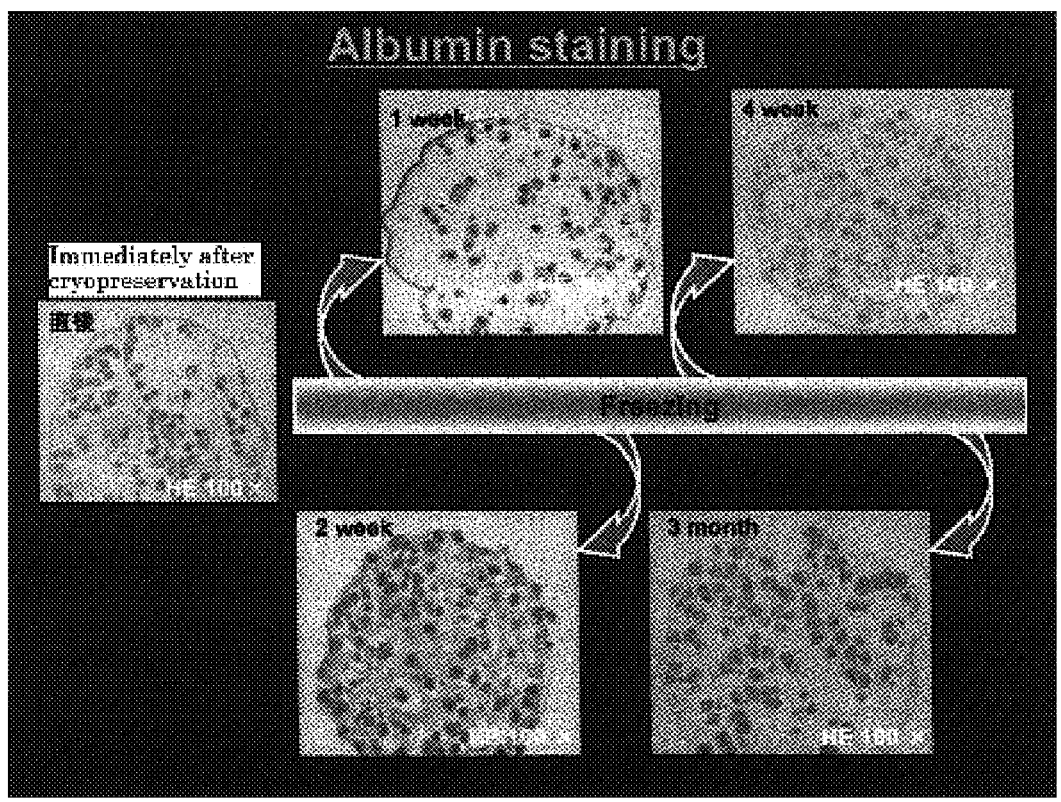
FIG. 2 gives albumin staining (ALB) test results with photographs, which show that cryopreserved cells produced albumin even three months later and that rat hepatocytes survived even after being cryopreserved even for 3 months.
Figure 3:
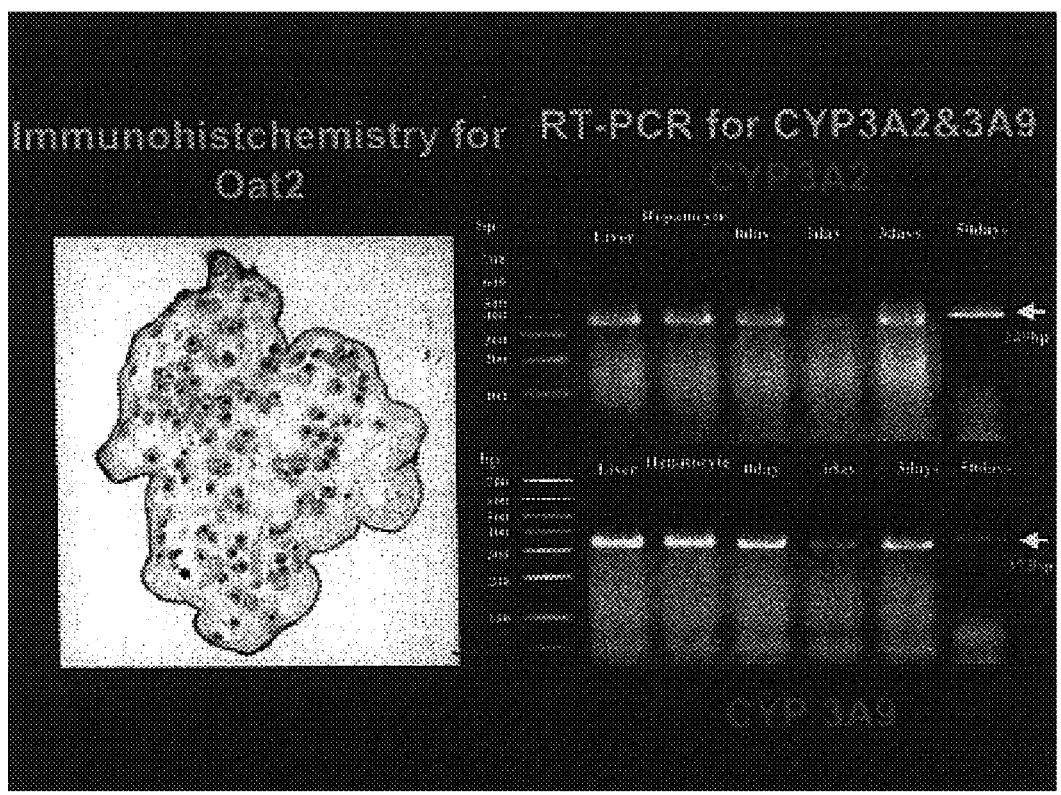
FIG. 3 shows that OAT2, CYP450III A2, 9 were exhibited as chemical-metabolizing indexes.

FIG. 1 shows H-E staining test results, which reveals that the rat hepatocytes in the immunoisolation membrane survived even after the cryopreservation for 90 days. FIG. 2 gives ALB test results with photographs, which show that cryopreserved cells produced albumin even three months later and that rat hepatocytes survived even after being cryopreserved even for 3 months. FIG. 3 shows that OAT2, CYP450IIIA2, 9 were exhibited as chemical-metabolizing indexes.

Experiment 2

The function of the rat hepatocytes in the immunoisolation membranes was histogentically evaluated with respect to specific hepatocyte-metabolizing capacity (albumin synthesis ability and urine nitrogen synthesis ability, H-E, PAS, ALB).

Figure 4:
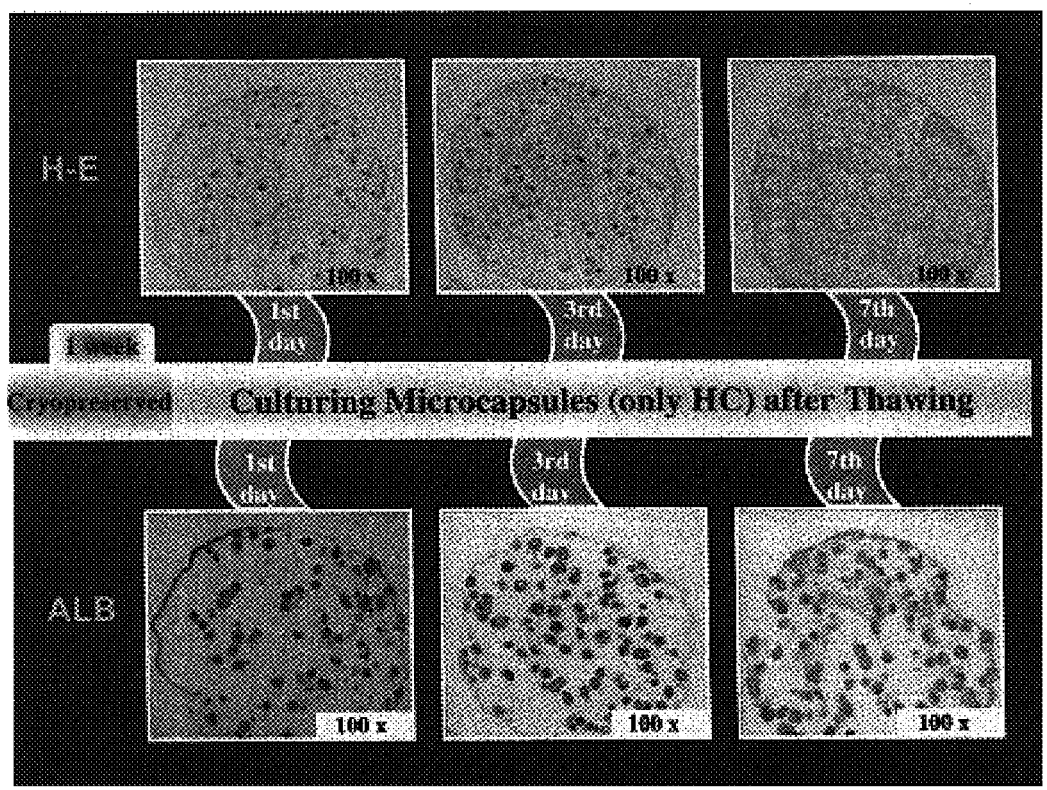
FIG. 4 shows H-E staining test results in an upper portion and ALB test results in an lower portion (1st day, 3rd day and 7th day from the left), revealing that the cryopreserved capsules maintained the metabolizing function peculiar to the liver even after one-week cultivation.

The immunoisolation membrane-enclosed cells cryopreserved for one week were unfrozen in water bath at 37° C., and cultured for one week. FIG. 4 shows results on this culturing. FIG. 4 shows H-E staining test results in an upper portion and ALB test results in an lower portion (1st day, 3rd day and 7th day from the left), revealing that the cryopreserved capsules maintained the metabolizing function peculiar to the liver even after one-week cultivation.

Figure 5:
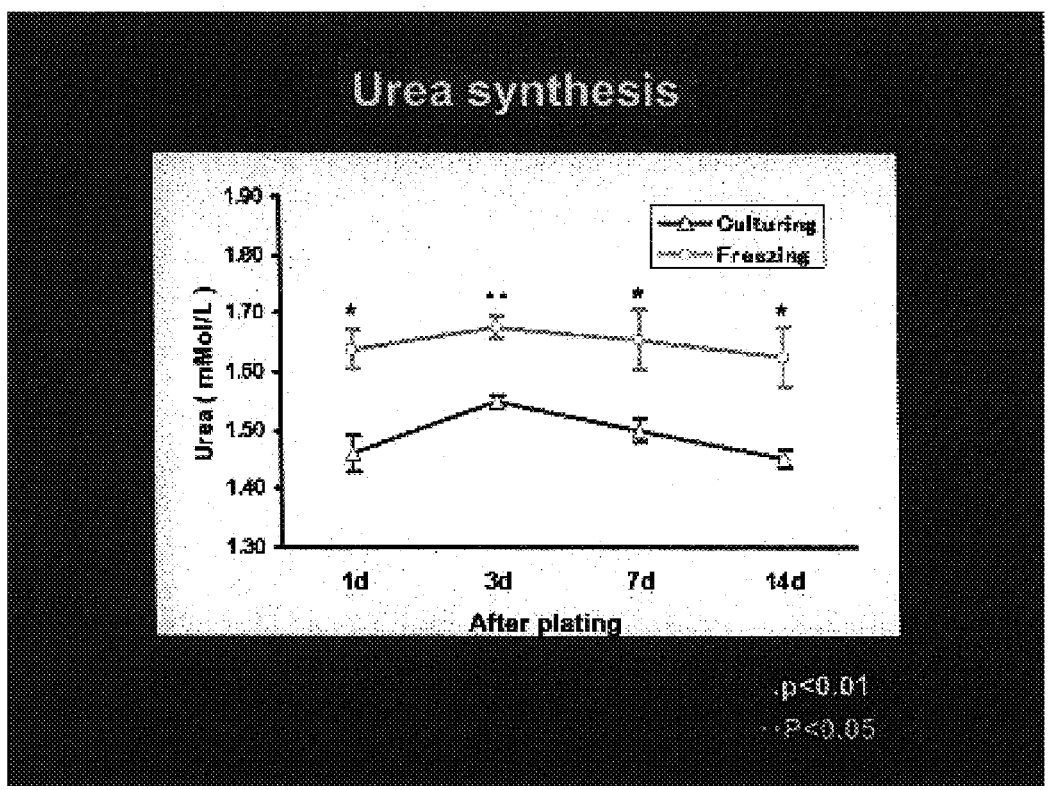
FIG. 5 shows results in observing synthesized amounts of urea during culturing, which demonstrates that the cryopreserved rat cells in the immunoisolation membranes exhibited higher urea synthesis and cell activity (an upper polygonal line in FIG. 5) in unfrozen culturing over a time period from 1st day to 14th days as compared with non-frozen rat cells (a lower polygonal lines in FIG. 5).

FIG. 5 shows results in observing synthesized amounts of urea during culturing, which demonstrates that the cryopreserved rat cells in the immunoisolation membranes exhibited higher urea synthesis and cell activity (an upper polygonal line in FIG. 5) in unfrozen culturing over a time period from 1st day to 14th days as compared with non-frozen rat cells (a lower polygonal lines in FIG. 5).

Experiment 3

The cryopreserved hepatocytes in the immunoisolation membranes originated from the primary human hepatocytes obtained in the same manner as in Experiment 1 were unfrozen in water bath at 37° C. The function of the rat hepatocytes in the immunoisolation membranes was histogentically evaluated with respect to specific hepatocyte-metabolizing capacity (albumin synthesis ability and urine nitrogen synthesis ability, H-E, PAS, ALB). It was examined whether the cryopreserved hepatocytes in the immunoisolation membranes functioned normally or not.

Figure 6:
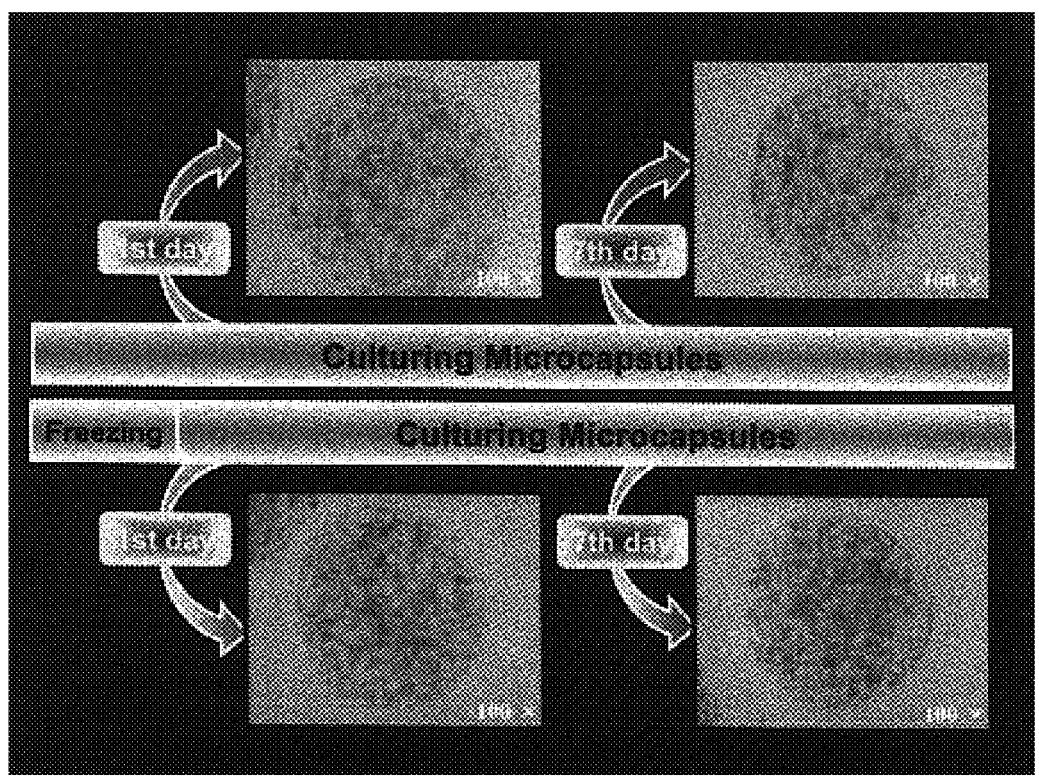
FIG. 6 gives photographs obtained by observing, with a phase microscope, preparations in which unfrozen human hepatocytes in an immunoisolation membrane was treated with formalin and fixed with paraffin, which shows that the shape of the human hepatocytes in the immunoisolation membrane did not change by freezing, unfreezing and culturing.
Figure 7:
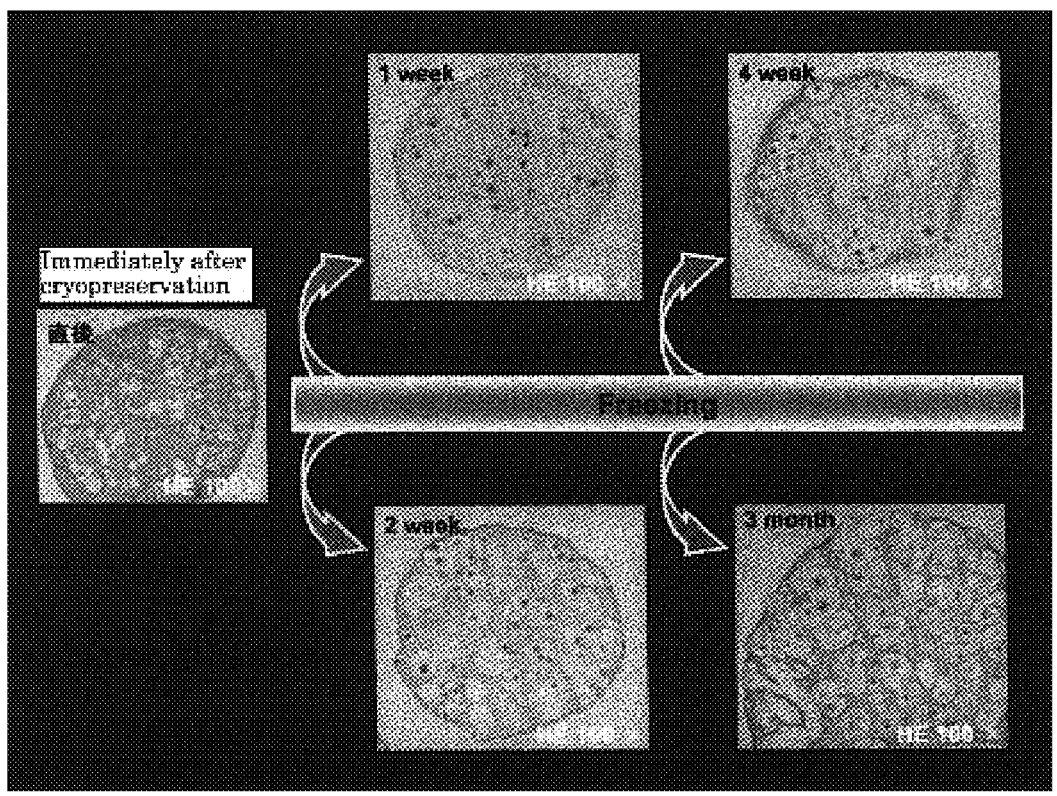
FIG. 7 gives photographs in H-E staining results of human hepatocytes in an immunoisolation membrane immediately after the preparation thereof and when unfrozen one week after, 2 weeks after, 4 weeks after and 3 months after the preparation, which shows that the unfrozen hepatocytes in the immunoisolation membranes survived when unfrozen one week after, 2 weeks after, 4 weeks after and 3 months after the preparation.
Figure 8:
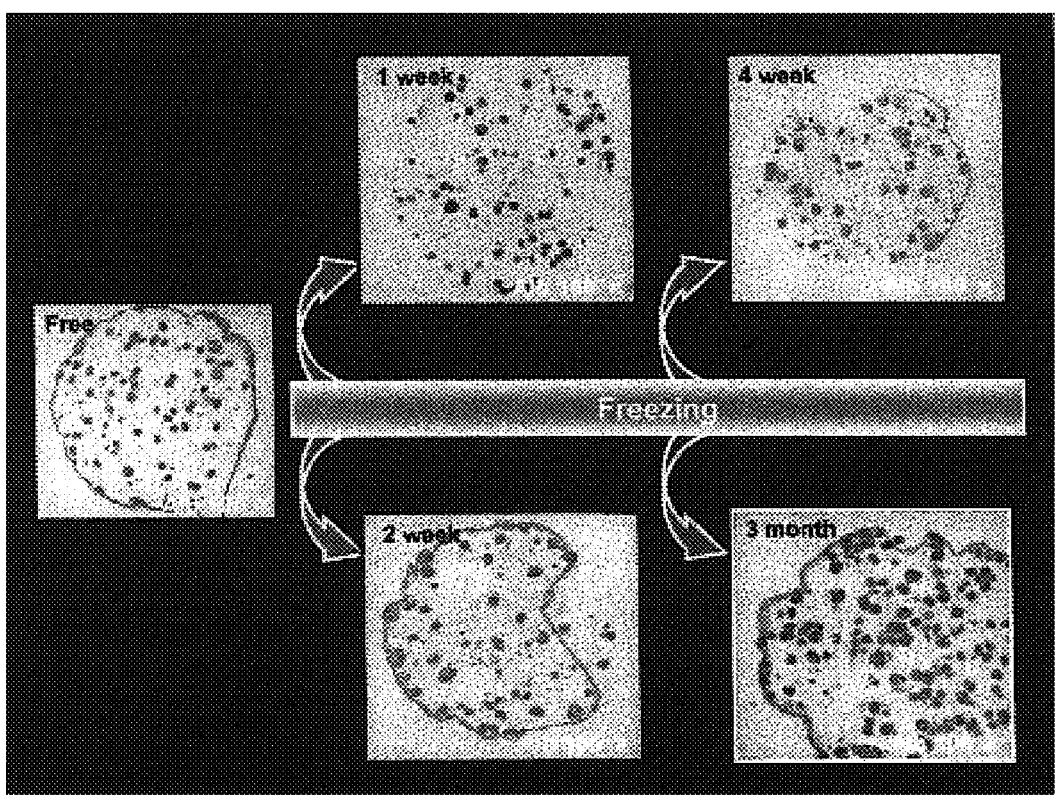
FIG. 8 gives photographs in ALB results of human hepatocytes in an immunoisolation membrane immediately after, one week after, 2 weeks after, 4 weeks after and 3 months after the preparation, which shows that the unfrozen hepatocytes in the immunoisolation membranes survived immediately after, one week after, 2 weeks after, 4 weeks after and 3 months after the preparation.

FIG. 6 gives photographs obtained by observing, with a phase microscope, preparations in which unfrozen human hepatocytes in an immunoisolation membrane was treated with formalin and fixed with paraffin, which shows that the shape of the human hepatocytes in the immunoisolation membrane did not change by freezing, unfreezing and culturing. FIG. 7 gives photographs in H-E staining results of human hepatocytes in an immunoisolation membrane immediately after the preparation thereof and when unfrozen one week after, 2 weeks after, 4 weeks after and 3 months after the preparation, which shows that the unfrozen hepatocytes in the immunoisolation membranes survived when unfrozen one week after, 2 weeks after, 4 weeks after and 3 months after the preparation. FIG. 8 gives photographs of ALB results of human hepatocytes in an immunoisolation membrane immediately after, one week after, 2 weeks after, 4 weeks after and 3 months after the preparation, which shows that the unfrozen hepatocytes in the immunoisolation membranes survived immediately after, one week after, 2 weeks after, 4 weeks after and 3 months after the preparation. From FIG. 7 and FIG. 8, it is shown the hepatocytes in the immunoisolation membranes unfrozen one week, two weeks, 4 weeks and 3 months after starting the cryopreserving survived and normally functioned.

Experiment 4

The enclosed hepatocytes in the immunoisolation membranes originated from the primary hepatocytes obtained in the same manner as in Experiment 1 were unfrozen in water bath at 37° C., and the activity of the hepatocytes in the immunoisolation membranes was examined. The unfrozen hepatocytes in the immunoisolation membranes were filled in a radial flow bioreactor (Able Co., Ltd.), and the specific hepatocyte-metabolizing capacity (urine nitrogen synthesis ability and ammonia-metabolizing ability) was examined histogenetically (H-E, ALB), and it was examined whether the cryopreserved hepatocytes in the immunoisolation membranes functioned normally.

Figure 9:
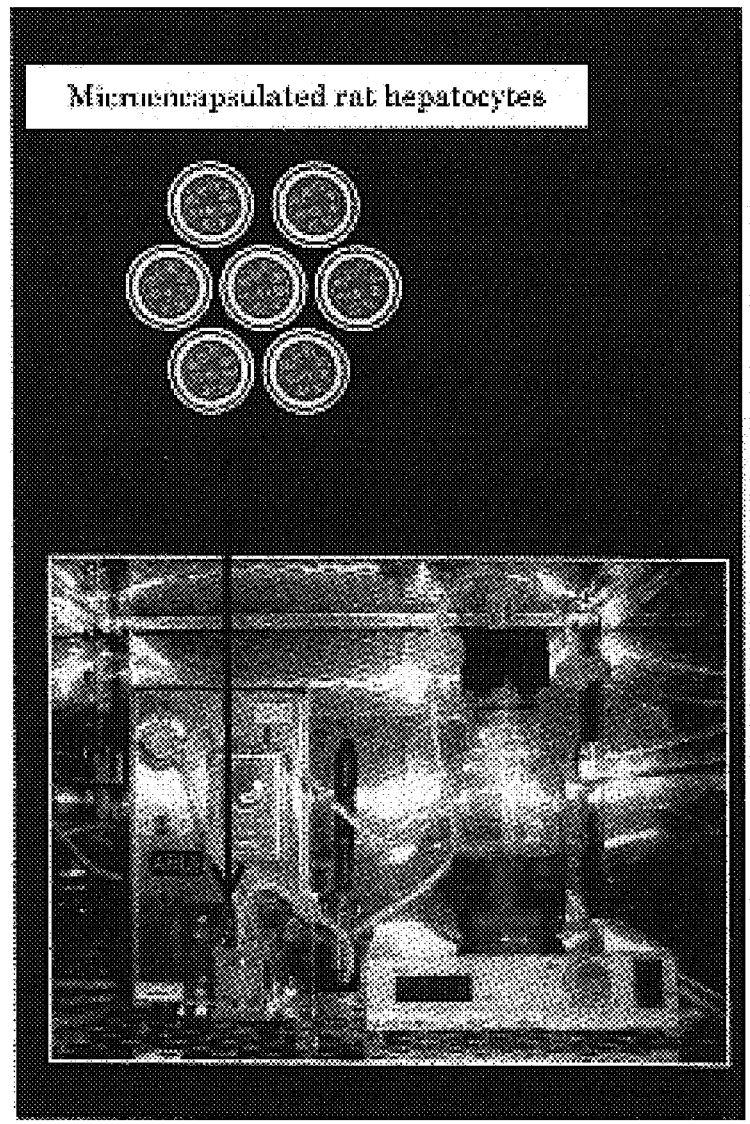
FIG. 9 shows a radial flow bioreactor (Able Co., Ltd.).
Figure 10:
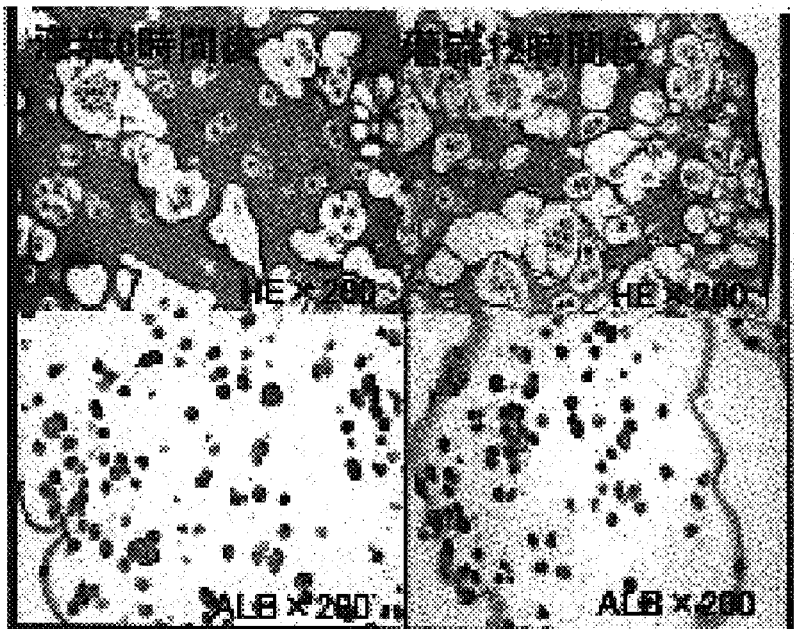
FIG. 10 gives H-E staining results and ALB results 6 hours, 12 hours, 24 hours and 72 hours after perfusion, which shows that the microencapsulated rat hepatocytes survived for 6 hours, 12 hours, 24 hours and 72 hours after perfusion.
Figure 10:
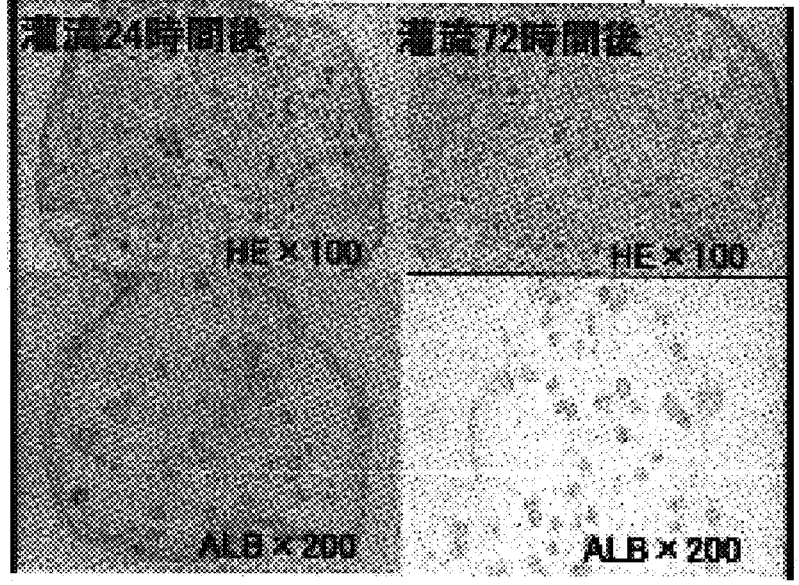
Figure 11:
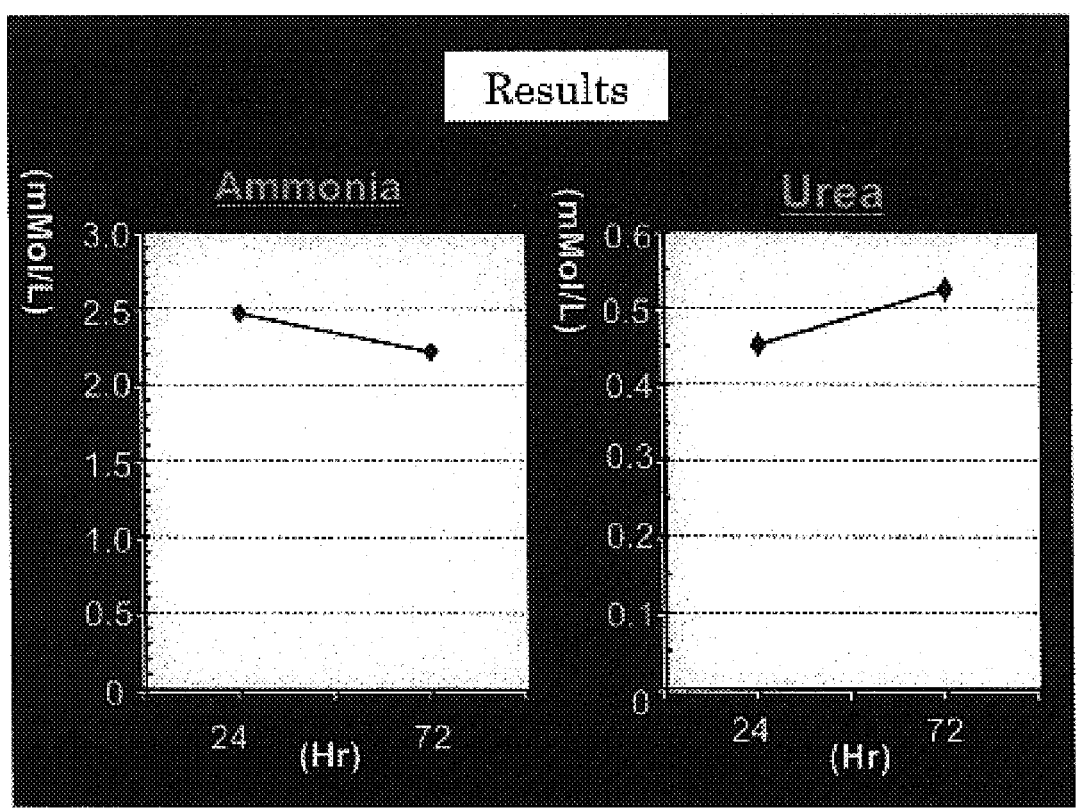
FIG. 11 gives results of synthesized amounts of ammonia and urea when perfused for 24 hours and 72 hours, which shows that the hepatocytes functioned normally.

FIG. 9 shows the radial flow bioreactor (Able Co., Ltd.). In FIG. 9, a solution on the right is a culture liquid, which was perfused through a pump and a tube. FIG. 10 gives H-E staining results and ALB results 6 hours, 12 hours, 24 hours and 72 hours after perfusion, which shows that the microencapsulated rat hepatocytes normally survived and functioned for 6 hours, 12 hours, 24 hours and 7.2 hours after perfusion. FIG. 11 gives synthesized amounts of ammonia and urea when perfused for 24 hours and 72 hours, which shows that the hepatocytes functioned normally.

The volume of the bioreactor was 5 cc, the filled amount of the hepatocytes was 3×107, and the culture liquid was flown at a flow rate of 4.5 cc/min. from an outer periphery toward a central portion of the bioreactor inside a $CO_2$ incubator at a temperature of 37° C. A culture liquid was DMEM reinforced with 10% FBS, 0.2% bovine serum albumin, 20 mM HEPES, 25 mM NaHCO3, 1 mg/ml galactose, 30 μg/ml L-proline, 0.5 mM glutamine, 10-7 M dexamethazone, 10 mM nicotinamide, 0.5 μg/ml ITS51500, 20 ng/ml EGF, 0.1 mM L-ascorbic acid 2-phosphate (Acs-2P), and 100 μg/ml penicillin, 50 μg/ml streptomycin.

What is claimed is:

1. A method for cryopreserving living animal cells in immunoisolation membranes, comprising:
   (1) cutting out a piece of a living organ from an animal,
   (2) digesting the cutout piece into discrete living animal cells and separating the discrete cells,
   (3) suspending the separated cells in a solution of sodium chloride containing sodium alginate and collagen to obtain a suspension comprising cells
   (4) forming microcapsules of the living animal cells by gelling the cell suspension,
   (5) forming immunoisolation membranes around an outer surface of each of the microcapsules of the cells by covering the outer surfaces with alginate-(poly-L-lysine) to obtain enclosed cells, which are enclosed in the immunoisolation membranes,
   (6) suspending the enclosed cells in a cell damage-preventing solution to obtain a microcapsule suspension, and
   (7) cryopreserving the microcapsule suspension with liquid nitrogen by freezing the microcapsule suspension in the liquid nitrogen within 10 minutes after suspending the cells in (6) above to cryopreserve the cells, thereby cryopreserving the cells.

2. The method of claim 1, wherein the living organ from an animal is a human liver or a rat liver.

3. The method of claim 1, wherein the cell damage-preventing solution is Dulbecco's modified Eagle medium (DMEM) containing fetal bovine serum (FBS) and dimethylsulfoxide (DMSO).

4. The method of claim 2, wherein the cell damage-preventing solution is Dulbecco's modified Eagle medium (DMEM) containing fetal bovine serum (FBS) and dimethylsulfoxide (DMSO).

* * * * *

UNITED STATES PATENT AND TRADEMARK OFFICE
CERTIFICATE OF CORRECTION

PATENT NO. : 7,553,612 B2 Page 1 of 1
APPLICATION NO. : 11/082055
DATED : June 30, 2009
INVENTOR(S) : Aoki et al.

It is certified that error appears in the above-identified patent and that said Letters Patent is hereby corrected as shown below:

On title page replace Item [75], to read as follows:
--[75] Inventors: Takeshi Aoki, Setagaya-ku (JP); Mitsuo Kusano, Ohta-ku (JP); Yoshinori Shimizu, Ohta-ku (JP); Tomotake Koizumi, Shinagawa-ku (JP); Daisuke Yasuda, Ohta-ku (JP); Yoshihiko Izumida, Chiyoda-ku (JP); Noriyuki Murai, Ohta-ku (JP); Zhenghao Jin, Shinagawa-ku (JP); Yasuna Kobayashi, Shinagawa-ku (JP); Hirohisa Kato, Shinagawa-ku (JP); Luchun Hua, Shanghai (CN)--

Signed and Sealed this

Twenty-second Day of December, 2009

David J. Kappos
*Director of the United States Patent and Trademark Office*